United States Patent [19]

Jones et al.

[11] Patent Number: 4,822,465
[45] Date of Patent: Apr. 18, 1989

[54] HYDROGEN SULPHIDE SENSOR

[75] Inventors: Eric Jones, Chelmsford; Alan M. Doncaster, Maldon, all of United Kingdom

[73] Assignee: English Electric Valve Company Limited, Essex, United Kingdom

[21] Appl. No.: 69,542

[22] Filed: Jun. 30, 1987

[30] Foreign Application Priority Data

Jul. 7, 1986 [GB] United Kingdom ................ 8616506

[51] Int. Cl.$^4$ ...................... C23C 14/00; G01N 31/00
[52] U.S. Cl. ................................ 204/192.1; 204/410; 204/431; 73/27 R
[58] Field of Search ................ 204/192.1, 1 T, 410, 204/431, 432; 73/27 R

[56] References Cited

U.S. PATENT DOCUMENTS

| | | | |
|---|---|---|---|
| 4,197,089 | 4/1980 | Willis | 23/232 E |
| 4,339,424 | 7/1982 | Jacobson et al. | 423/58 |
| 4,453,151 | 6/1984 | Leary | 338/34 |

FOREIGN PATENT DOCUMENTS 1204708 9/1970 United Kingdom .
1527406 10/1978 United Kingdom .
2137356 10/1984 United Kingdom .

Primary Examiner—Donald L. Walton
Attorney, Agent, or Firm—Lowe, Price, LeBlanc, Becker & Shur

[57] ABSTRACT

Hydrogen Sulphide is a toxic gas present in many environments. It is necessary for a detector to be highly sensitive and not to respond to other common gases. The sensor is made up of electrodes (5) coated with a thin layer (6) of material comprising the oxides of molybdenum and tungsten and in the presence of hydrogen sulphide gas, changes its resistance. The layer is formed in such a way that a bronze-like ordered lattice is formed, containing molybdenum, tungsten and oxygen ions.

11 Claims, 3 Drawing Sheets

HYDROGEN SULPHIDE SENSOR

This invention relates to a Hydrogen Sulphide (H₂S) sensor.

Hydrogen sulphide is a toxic gas which may be present in many environments, in particular in the petrochemical industries. Since hydrogen sulphide $H_2S$ has a threshold level value (TLV) of 10 parts per million (ppm) and a short term exposure limit (STEL) of 15 ppm then H₂S sensors require high sensitivity to fairly low levels of the gas and must also be able to discriminate H₂S from other gases which may be present and not give spurious readings affected by such other gases.

One of the earliest and most simple forms of gas detection involved the use of live animals, such as canaries, which were taken into the environment to be monitored and any changes in their well-being noted and assumed to be due to the presence of unwanted gases. A canary will however fall foul to many different types of toxic gases and use of live animals is perhaps not suited to the modern requirements of gas detection.

More recently, solid state sensors have been commonly employed which rely on the change in resistance or conductance of some materials when certain gases are present. Materials are chosen which respond in known manner to a certain gas, and changes in their electrical resistance are noted. However, many of these materials have deficiencies, particularly in being sensitive to gases other than hydrogen sulphide. Such materials are not suitable for environments where other reducing gases are normally present and the user is only interested in knowing the concentration of hydrogen sulphide in the atmosphere.

The present invention provides an improved, highly selective, material for use in hydrogen sulphide detection which works on the changing resistance principle.

According to the present invention there is provided a hydrogen sulphide sensor including a sensing element comprising an ordered lattice containing molybdenum, tungsten and oxygen ions and electrical means for passing current through the element.

In a preferred embodiment of the invention the electrical means are a pair of interdigitated electrodes mounted upon an insulating substrate which is typically alumina. The sensing element may be a thin film deposited over the electrodes such that it covers and is in contact with them. The film may be deposited by sputtering or other techniques. A heater may be included for adjusting the temperature of the apparatus since the response of the molybdenum/tungsten oxide film will vary with temperature. A heating element may be placed on the under side of the alumina block and the electrodes and sensing film mounted on the other side.

Alternatively, the alumina substrate could be provided in the form of a cylinder with a heating element embedded within and an electrode structure fixed to the outside.

Although the oxides of both tungsten and molybdenum are known to have resistive properties which vary with the ambient level of H₂S, it has been found that a lattice combining the two has unexpectedly high response and clearing rates, as will be further shown below, and hence is well suited for use in a hydrogen sulphide sensor.

A typical sputtering technique used in embodiments of the invention results in an ordered structure of molybdenum, tungsten and oxygen ions which is different to a simple mixture and leads to an increase in electron mobility throughout the lattice. The ordered structure is thus similar to a bronze.

Embodiments of the invention are now further described, by way of example only, with reference to the accompanying drawings, in which.

Figure 4:
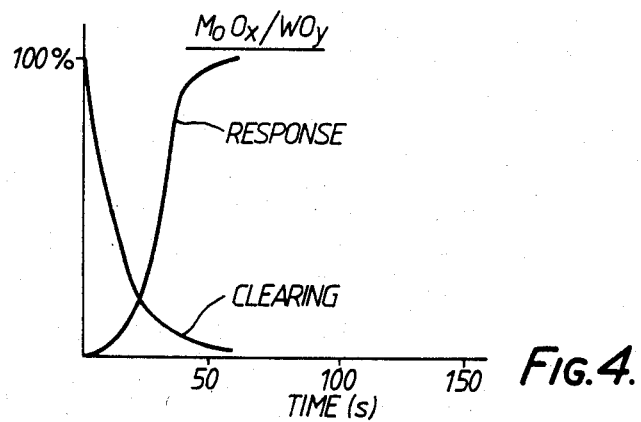
Figure 5:
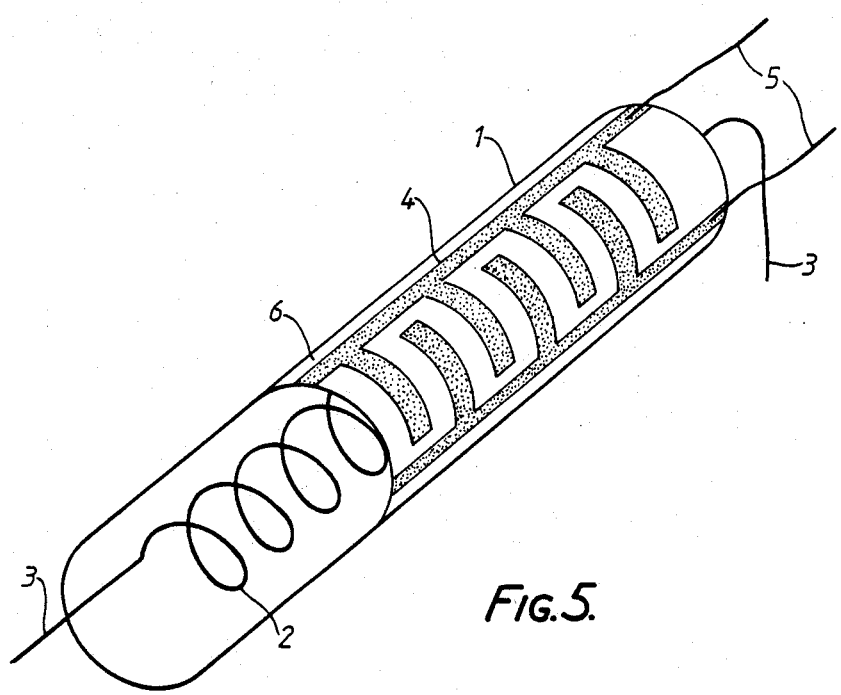

FIGS. 3a and b show typical response and clearing characteristics for a molybdenum oxide sensor and also a tungsten oxide sensor;

FIG. 4 shows the response and clearing characteristics of a sensor according to the present invention; and FIG. 5 is a partially cut-away view of a second sensor in accordance with the invention.

Figure 1:
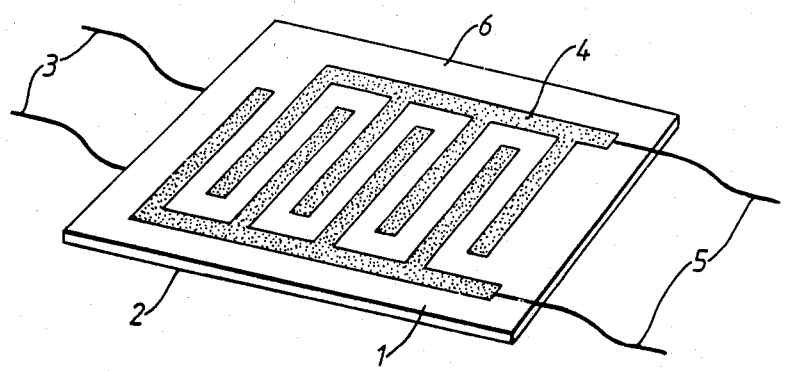
FIG. 1 shows a sensor in accordance with the invention.

Referring to FIG. 1, a hydrogen sulphide sensor comprises an alumina substrate 1 underneath which is affixed a heater 2 and electrical connections 3 to the heater. Upon the upper side of the alumina substrate 1 is fixed an interdigitated array of conducting electrodes 4 together with their associated electrical connections 5. A thin film 6 containing a mixture of oxides of molybdenum and tungsten is deposited on the upper side of the substrate such that it covers and is in contact with the electrode array 4.

The sensing film is deposited by a sputtering and oxidizing technique. Firstly, a layer of molybdenum sulphide, $M_oS_2$, of thickness about 1000 Å is sputtered over the alumina substrate and electrodes and subsequently a layer of tungsten oxide, WOx of the same thickness is sputtered on. The resulting film is then heated in air for several hours at a temperature of around 500° C. This has both a sintering and oxidizing effect and generates a complex combination of oxides of the metals. This combination does not consist merely of separate oxides of tungsten and molybdenum, but instead an ordered structure is formed which is an inseperable combination of the oxides and is in effect a type of crystal structure having both types of oxide contained within the same crystal lattice. This is similar to the type of structure observed in a bronze. The word bronze is accordingly used in this specification as a convenient way of describing this structure.

Figure 3:
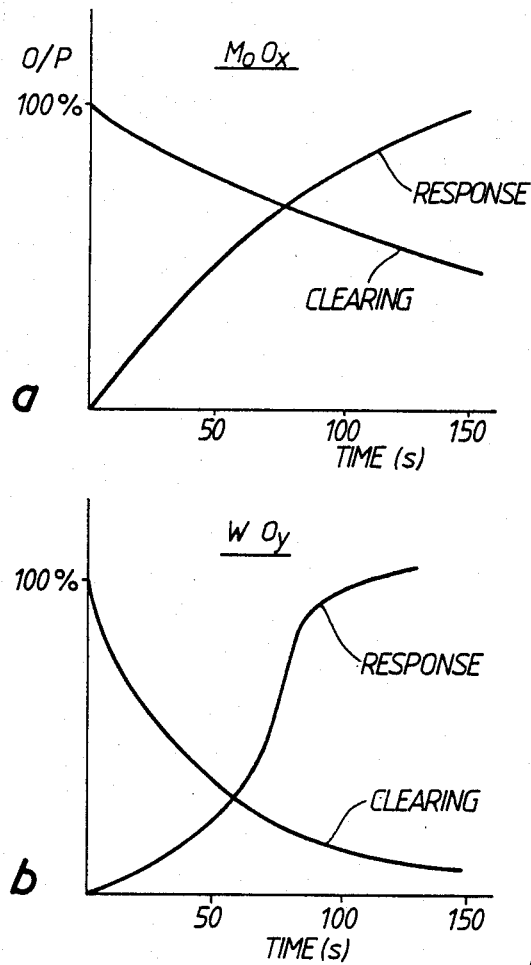

A comparison of FIGS. 3 and 4 shows the significant improvements in response and clearing time that can be achieved with the film composition of the present invention. FIGS. 3a and b show typical response and clearing times for respectively a molybdenum oxide, MoOx film and a tungsten oxide, WOy film, when exposed to hydrogen sulphide in a concentration of 35 ppm. It is seen that both films have a poor response rate and take well over 50 seconds to reach even 50% of their maximum output, for that concentration.

FIG. 4 shows the response and clearing curves for the combined MoOx/WOy film under the same conditions. It is clearly seen that the response and clearing times are both noticeably quicker than for sensing elements composed of the oxides of one metal only and that the improvement is more than would be expected were the film made simply from a mixture of molybdenum and tungsten oxides which are not combined to form a composite structure.

Figure 2:
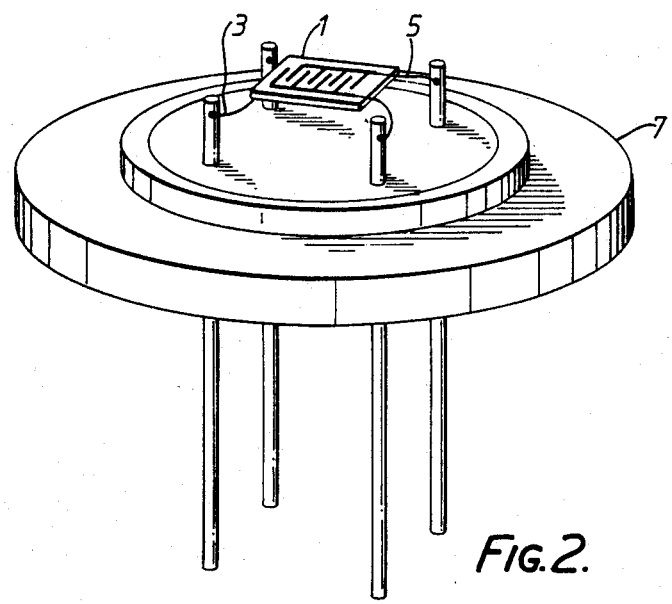
FIG. 2 shows the sensor of FIG. 1 attached to a typical mounting fixture.

In use, a sensing element as shown in FIG. 1 may be mounted on a suitable 4-pin header 7, as shown in FIG. 2, for mounting on a printed circuit board. FIG. 2 also indicates the approximate size of the sensor since the 4-pin header is about the size of a typical transistor can and hence the sensing element will have a length and width of perhaps a few millimeters.

Current is passed to the heating coils 3 by means of two of the pins on header 7 and to the electrode connections 5 through the remaining two pins. The electrode connections 5 are connected to a standard circuit (not shown) responsive to changes in the resistance of the sensing film 6 and which may be calibrated to directly read out the concentration of hydrogen sulphide in the atmosphere.

FIGS. 3 and 4 show the characteristics for various sensors with one particular ambient concentration of $H_2S$. It is found that the response of the combined molybdenum/tungsten oxide sensor is related to the concentration of $H_2S$ by a logarithmic function. As the log of the concentration increases so the log of the resistance of the sensing film decreases.

The sensing films response to hydrogen sulphide is also a function of temperature and insufficient sensitivity is achieved at room temperature. Hence the heating element 2 is operated to obtain a working temperature of around 200°–300° C. although this level can of course vary depending upon the conditions required at the time.

It is important that a hydrogen sulphide sensor should not respond significantly to other gases which may be present and hence give false readings. The sensing film of the present invention has been found to be eminently suitable for this and gives very little response to interfering gases, as is shown in Table 1 below.

TABLE 1

| Interfering Gas | Equivalent H S Response ppm |
|---|---|
| 1000 ppm Ethanol | 1.5 |
| 1000 ppm Octane | 0.5 |
| 1% Methane | 0.2 |
| 0.5% Hydrogen | 0.1 |
| 1000 ppm Acetone | 0.2 |
| 50 ppm Ammonia | 0.1 |
| 1000 ppm Ammonia | 0.1 |
| 50 ppm HexaMethylDiSiloxane | 0.2 |

It is seen from the table that the sensing element is only slightly affected by high concentrations of the other common gases which may be found in environments alongside hydrogen sulphide. Hexa Methyl Di Siloxane is a poison which may be found in a petrochemical environment and it is particularly important that detection of hydrogen sulphide is not interfered with by this chemical.

FIG. 5 shows an alternative embodiment of the invention in which the alumina substrate 1 is in the form of a cylinder. A heating element 2 is coiled within and throughout the length of the cylinder and the electrodes are deposited around the outside. The film is then deposited over the alumina cylinder and electrodes. The functioning of the alternative structure is identical to that of the planar structure described above and the cylindrical sensor may be useful in environments where a planar-like sensor is not suitable. Several different configurations can be envisaged for sensors embodying the present invention.

We claim:

1. A hydrogen sulphide sensor including a sensing element comprising an ordered lattice containing only molybdenum, tungsten and oxygen ions; and electrical means for passing electric current through the element.

2. A hydrogen sulphide sensor as claimed in claim 1 wherein the electrical means includes a pair of electrodes deposited on an insulating substrate and the sensing element is a thin film covering the electrodes and making a conductive path between them.

3. A hydrogen sulphide sensor as claimed in claim 2 wherein the electrodes form an interdigitated array.

4. A hydrogen sulphide sensor as claimed in claim 1 including heating means to control the temperature of the sensing element.

5. A method of fabricating a hydrogen sulphide sensor including the step of depositing two or more compounds, each containing at least one of molybdenum, tungsten and oxygen, over a substrate in such a manner that a thin film is formed, having an ordered lattice structure of only molybdenum, tungsten and oxygen ions.

6. A method as claimed in claim 5 wherein the compounds are deposited in such a manner that a bronze-like structure is formed.

7. A method as claimed in claim 5 wherein a first layer containing a first compound is deposited over a substrate and a second layer containing a second compound is deposited over the first layer, each compound containing at least one of molybdenum, tungsten and oxygen.

8. A method as claimed in claim 7 wherein layers of molybdenum sulphide and tungsten oxide are sputtered on to the substrate and the resulting combination is heated, in the presence of oxygen, for a chosen period of time at a chosen temperature.

9. A method as claimed in claim 8 wherein the combination is heated at 500° C.

10. A hydrogen sulphide sensor, including a sensing element fabricated by the method of claim 5.

11. A hydrogen sulphide sensor, including a sensing element fabricated by the method of claim 8.

* * * * *